United States Patent
Matov et al.

(10) Patent No.: US 10,493,246 B2
(45) Date of Patent: Dec. 3, 2019

(54) SIDE BRANCH BALLOON

(75) Inventors: Nadia P. Matov, San Jose, CA (US);
Jayson De Los Santos, Pinole, CA (US); Guillermo Piva, San Ramon, CA (US); Tanhum Feld, Moshav Merhavya (IL); Eitan Konstantino, Orinda, CA (US)

(73) Assignee: TriReme Medical, Inc., Pleasanton, CA (US)

(*) Notice: Subject to any disclaimer, the term of this patent is extended or adjusted under 35 U.S.C. 154(b) by 2118 days.

(21) Appl. No.: 12/795,911

(22) Filed: Jun. 8, 2010

(65) Prior Publication Data

US 2011/0144583 A1 Jun. 16, 2011

Related U.S. Application Data

(60) Provisional application No. 61/185,124, filed on Jun. 8, 2009.

(51) Int. Cl.
*A61M 29/02* (2006.01)
*A61M 25/10* (2013.01)
*A61M 25/00* (2006.01)
*A61F 2/958* (2013.01)
(Continued)

(52) U.S. Cl.
CPC ........ *A61M 25/10* (2013.01); *A61M 25/0068* (2013.01); *A61M 25/104* (2013.01); *A61F 2/958* (2013.01); *A61F 2002/061* (2013.01); *A61F 2002/9583* (2013.01); *A61M 25/0108* (2013.01); *A61M 2025/0059* (2013.01); *A61M 2025/1045* (2013.01); *A61M 2025/1068* (2013.01);
(Continued)

(58) Field of Classification Search
CPC ............ A61M 25/0068; A61M 25/008; A61M 2025/1093; A61M 2025/0059; A61M 25/10; A61M 25/104; A61M 2025/0098; A61M 2025/1079; A61M 25/0108; A61M 2025/1068; A61M 2025/1081; A61F 2/958
USPC ... 604/103.05, 96.01, 103.09, 103.1, 103.13; 606/192, 194; 623/1.11
See application file for complete search history.

(56) References Cited

U.S. PATENT DOCUMENTS

| | | |
|---|---|---|
| 3,884,242 A | 5/1975 | Bazell et al. |
| 4,994,032 A | 2/1991 | Sugiyama et al. |
| 5,116,318 A | 5/1992 | Hillstead |

(Continued)

FOREIGN PATENT DOCUMENTS

| | | |
|---|---|---|
| EP | 0553960 A1 | 8/1993 |
| EP | 1 836 998 A1 | 9/2007 |

(Continued)

OTHER PUBLICATIONS

International Search Report and Written Opinion of PCT Application No. PCT/US2010/037818, dated Aug. 3, 2010, 7 pages total.

(Continued)

*Primary Examiner* — Katherine M Rodjom
(74) *Attorney, Agent, or Firm* — Wilson Sonsini Goodrich and Rosati, P.C.

(57) ABSTRACT

An improved balloon catheter structure includes a beveled distal tip, a reinforced distal portion, and an elastic or split sleeve over at least a portion of the balloon. The balloon may have a short length and a marker at its midline. The catheters are particularly useful for crossing through stent walls at vessel bifurcations.

22 Claims, 4 Drawing Sheets

(51) Int. Cl.
*A61F 2/06* (2013.01)
*A61M 25/01* (2006.01)

(52) U.S. Cl.
CPC .............. *A61M 2025/1079* (2013.01); *A61M 2025/1081* (2013.01); *A61M 2025/1093* (2013.01)

(56) References Cited

U.S. PATENT DOCUMENTS

| | | | |
|---|---|---|---|
| 5,295,962 A | 3/1994 | Crocker et al. | |
| 5,324,261 A | 6/1994 | Amundson et al. | |
| 5,454,788 A * | 10/1995 | Walker ................... | A61L 29/04 604/103 |
| 5,628,755 A | 5/1997 | Heller et al. | |
| 5,669,932 A | 9/1997 | Fischell et al. | |
| 5,827,231 A | 10/1998 | Harada | |
| 5,843,027 A | 12/1998 | Stone et al. | |
| 5,967,988 A | 10/1999 | Briscoe et al. | |
| 5,997,487 A | 12/1999 | Kolehmainen et al. | |
| 6,010,449 A | 1/2000 | Selmon et al. | |
| 6,030,405 A | 2/2000 | Zarbatany et al. | |
| 6,068,634 A | 5/2000 | Lorentzen et al. | |
| 6,120,523 A | 9/2000 | Crocker et al. | |
| 6,206,852 B1 | 3/2001 | Lee | |
| 6,540,721 B1 | 4/2003 | Voyles et al. | |
| 6,679,871 B2 | 1/2004 | Hahnen | |
| 6,679,900 B2 | 1/2004 | Kieturakis et al. | |
| 6,692,483 B2 * | 2/2004 | Vardi et al. ................... | 604/529 |
| 6,695,863 B1 | 2/2004 | Ramzipoor et al. | |
| 6,699,273 B2 | 3/2004 | Langan | |
| 6,796,960 B2 | 9/2004 | Cioanta et al. | |
| 6,830,575 B2 | 12/2004 | Stenzel et al. | |
| 6,884,258 B2 | 4/2005 | Vardi et al. | |
| 6,966,902 B2 | 11/2005 | Tsugita et al. | |
| 6,994,687 B1 | 2/2006 | Shkolnik | |
| 7,022,106 B2 | 4/2006 | Jorgensen | |
| 7,273,470 B2 | 9/2007 | Wantink | |
| 7,306,575 B2 | 12/2007 | Barbut et al. | |
| 7,491,213 B2 | 2/2009 | Perreault et al. | |
| 7,635,347 B2 | 12/2009 | Kastenhofer | |
| 2001/0021840 A1 | 9/2001 | Suresh et al. | |
| 2003/0014070 A1 | 1/2003 | Meens | |
| 2004/0186560 A1 | 9/2004 | Alt | |
| 2005/0015108 A1 * | 1/2005 | Williams et al. ............. | 606/194 |
| 2005/0055077 A1 * | 3/2005 | Marco ............ | A61B 17/320725 623/1.11 |
| 2005/0075711 A1 | 4/2005 | Neary | |
| 2005/0107821 A1 * | 5/2005 | Shanley ................ | A61M 25/10 606/194 |
| 2005/0203463 A1 | 9/2005 | Lampropoulos | |
| 2005/0216047 A1 * | 9/2005 | Kumoyama ...... | A61M 25/1027 606/191 |
| 2006/0100694 A1 | 5/2006 | Globerman | |
| 2006/0224113 A1 * | 10/2006 | van Sloten ........ | A61M 25/0009 604/103.1 |
| 2008/0045896 A1 | 2/2008 | Yribarren et al. | |
| 2009/0024212 A1 | 1/2009 | Siess et al. | |
| 2009/0048655 A1 | 2/2009 | Jang | |
| 2009/0112159 A1 | 4/2009 | Slattery et al. | |
| 2010/0010303 A1 | 1/2010 | Bakos | |
| 2015/0066070 A1 | 3/2015 | Matov et al. | |

FOREIGN PATENT DOCUMENTS

| | | |
|---|---|---|
| EP | 1894595 A1 | 3/2008 |
| JP | H05337189 A | 12/1993 |
| JP | H07231941 A | 9/1995 |
| JP | 2006334222 A | 12/2006 |
| JP | 2008513125 A | 5/2008 |
| JP | 2012514235 A | 6/2012 |
| WO | WO 96/19256 A1 | 6/1996 |
| WO | WO 98/06452 A1 | 2/1998 |
| WO | WO-2006034008 A2 | 3/2006 |
| WO | WO-2010144483 A1 | 12/2010 |

OTHER PUBLICATIONS

European search report and opinion dated Oct. 23, 2013 for EP Application No. 10786711.1.
Office action dated Dec. 17, 2014 for U.S. Appl. No. 14/546,696.
Office action dated Apr. 2, 2015 for U.S. Appl. No. 14/546,696.
Office action dated Aug. 14, 2015 for U.S. Appl. No. 14/546,696.

* cited by examiner

SIDE BRANCH BALLOON

CROSS-REFERENCES TO RELATED APPLICATIONS

This application claims the benefit of provisional application No. 61/185,124, filed on Jun. 8, 2009, the full disclosure of which is incorporated herein by reference.

BACKGROUND OF THE INVENTION

1. Field of the Invention

The present invention relates to medical methods and devices, more specifically to medical dilatation balloon catheters.

Balloon catheters often need to cross through luminal obstructions, such as stent struts, occlusions, and tight turns. One particular obstructions is encountered when treating stenosis present at an arterial bifurcation. Treatment of a bifurcation site is challenging since they are Y-shaped and require a different approach from a simple lesion treated with a regular cylindrical stent. When treating stenosis at bifurcation, it is common practice to use a conventional cylindrical stent and, after implantation, manipulate the stent's geometry using a balloon catheter to accommodate the bifurcated anatomy.

The usual practice is to place a cylindrical stent in the main vessel across the bifurcation ostium which typically results in partially blocking ("jailing") the side branch ostium with stent struts. The struts may be opened by advancing an angioplasty balloon over a guide wire through the stent struts so that a distal portion of the balloon is inside the side branch. If all goes well, the balloon may then be inflated to open struts and clear the ostium. Optionally, if the side branch is diseased or not expanded widely enough, a second stent may be delivered into the side branch and placed with its proximal end as close as possible to the main vessel stent in an attempt to place the stents in a Y-pattern.

Crossing into the side branch with an angioplasty balloon, however, can be difficult. The catheter tip and/or balloon that is threaded on a guide wire is often caught by the stent struts and the catheter cannot be advanced. This phenomenon is enhanced because the guide wire always has bias and is leaning on the nearest stent strut. The distal tips of balloon catheters are not designed to pass obstructions such as stent struts. The tips are usually soft and atraumatic to provide smooth passage without scratching the artery walls during delivery. Soft tips are prone to deformation and are more difficult to push past struts and other obstructions. The clearance between the catheter tip and the guidewire is usually large, again exacerbating the difficulty of pushing the tip past obstructions.

Conventional balloon catheter shafts are not designed to transmit torque, particularly over their distal segments near the balloon. Often, the distal-most 25-30 cm of the shaft is made from a soft, low profile and thin wall polymer material which is very ineffective for torque transmission. In addition, the majority of the torque is lost in the inflatable shell or the balloon which is made of a thin polymer shell (typically nylon or pebax) and is floating over the distal end of the catheter. Attempts to rotate the catheter will result in twisting of the polymer shaft followed by unfolding of the balloon pleats (referred to a the "candy wrapper effect") and increasing profile and risk of damaging the catheter without meaningful torque transmission to the tip. Therefore, when the catheter tip is caught in a stent strut or other obstruction, the operator can only move the catheter back and forth, poking the strut and hoping that the catheter will somehow be able to overcome and cross it. This process is unpredictable and uncontrolled, both in terms of success and of the possible damage caused. Inability to cross is documented in the literature and is a common issue in bifurcations and other occlusions.

The outer surface of a conventional folded balloon can also catch on stent struts. Angioplasty balloons are folded in order to assume a small diameter for delivery. These folds or pleats often catch on stent struts if advanced through a cell. The tendency of the balloon to catch is worsened when the catheter turns from the main vessel into the side branch, causing the balloon to bend and partially unwrapping the pleats. In some cases the balloon tip may also bend and twist, further hindering the progress of the catheter.

When treating bifurcations, it is common practice to dilate the side-branch ostium. Clinical studies have shown a high correlation between post procedure (acute) ostium size and long term patency of the side branch vessel. However, large ostium dilations are not easily achieved. Measurements of human bifurcation anatomy show that the ostium size is significantly bigger than the side branch diameter. For side branch vessels between 2.5 to 3.0 mm diameters, the ostium is usually about 0.5 mm bigger. When using a regular sized balloon, the difference in diameter between the side-branch ostium and the side-branch can result in either over expansion in the side branch causing injury to the side branch or under-deployment in the ostium. Often a "kissing balloon" technique is performed where two balloons are deployed in the main vessel. Two balloons, however, can cause anatomical deformation and excessive pressure in the main vessel. Furthermore, struts and other stent components are not advantageously placed. While short balloons could alleviate these problems, a short balloon would have a tendency to slip and lose its longitudinal position in the vessel. Therefore, dilation balloons are typically at least 8 mm in length or are provided with external blades or cages to prevent slippage.

A balloon catheter addressing some of the issues noted above will be desirable. In particular, it would be desirable to provide a balloon catheter with improved crossability achieved through adding another degree of control to the operator and a new dimension to the procedure by adding asymmetric tip design such as skived, beveled or similar configuration that can be re-oriented by rotation when facing an obstacle. Enhanced torqueability is a key element of such balloon catheter.

2. Description of the Background Art

Catheters having beveled or chamfered distal tips are described in U.S. Pat. Nos. 3,884,242; 5,967,988; 6,010,449; 6,206,852; 6,966,902; and 7,306,575 and in U.S. Publ. Application No. 2009/024212. Balloon and other catheters having torsionally reinforced distal ends are described in U.S. Pat. Nos. 4,994,032; 5,827,231; 5,997,487; 6,994,687; and 7,022,106. Catheters having "short" balloons and having balloons with mid-line markers are described in U.S. Pat. Nos. 5,295,962; 5,324,261; 5,669,932; 6,692,483; and 6,884,258; and in U.S. Publ. Application Nos. 2004/186560; 2006/100694; 2008/045896; and 2009/048655. Catheters having sleeves over at least a portion of an angioplasty or other balloon are described in U.S. Pat. Nos. 5,628,755; 6,068,634; 6,679,900; 6,695,863; 6,699,273; and 6,830,575; and U.S. Publ. Application Nos. 2005/203463 and 2009/112159.

BRIEF SUMMARY OF THE INVENTION

This invention provides balloon catheters having improved "pushability" (column strength and asymmetric tip design) and torqueability (torsional stiffness), particularly through the distal balloon section. The balloon catheters of the present invention have an improved ability to cross obstacles and obstructions, such as stent struts and tight turns with improved physician control, improved ostium expansion, and reduced injury to the vasculature using the benefits of asymmetric tip design coupled with torque transmission properties. Such balloon catheters are useful for a variety of cardiology procedures, including angioplasty, drug delivery, stent deployment, and the like, and have particular advantages when employed vascular bifurcations.

In one embodiment, the balloon catheter tip is formed in asymmetric manner (e.g. beveled, asymmetrically tapered, differential stiffness across the circumference of the tip) to allow improved crossability overcoming obstacles, such as stent struts, by rotating and realigning the asymmetric tip relative to the obstruction. By "beveled", it is meant that the distal tip of the catheter has a at least one planar or non-planar surface at its leading end, where at least a portion of the surface is at a non-perpendicular angle relative to the axis of the catheter body typically from 30° to 70°. Usually, the leading end is formed by a planar "cut" across the distal tip. In other cases there may be two or more planar cuts to form facets, each of which is at an angle relative to the axis of the catheter body. In other instances, the beveled end could have one or more non-planar surfaces or facets, at least some of which are inclined relative to the catheter body axis.

In one embodiment, the balloon catheter shaft is designed to transmit torque applied by an operator so that the distal tip can be rotated. Combination of the beveled tip and improved torsional stiffness (torque transmission) improves the crossing properties more than either feature alone.

In one embodiment, the balloon catheter comprises a "torque bridge" to allow torque delivery through the balloon region of the catheter body. The torque bridge can be in a form of cylindrical polymer sleeve disposed over or attached to at least a portion of the balloon and covering the balloon taper and all or part of the balloon working length. Such sleeves can cause the balloon to progressively inflate from the proximal end toward the distal end, which can be advantageous in opening stent cells. Such torque bridge can take other forms, as well, such as metal reinforcement for the proximal balloon segment or welding of the inner member to the balloon proximal leg to improve structural stability during rotation.

The torque bridge of the present invention increases rotational accuracy and stent deployment precision by minimizing uncontrolled rotation resulting from "unwinding" of the catheter or portions thereof during balloon inflation and stent deployment. The torque bridge of the present invention enhances the ability of the stent to rotate since the system does not absorb torque. Torque absorption in the prior art is sometimes caused by windup of catheter components such as balloon folds, distal shaft and, for catheters having two guidewires side branch wire lumen wrap on the main vessel wire lumen and others. In one embodiment of the present invention, the torque bridge is used to enhance rotation and/or self rotation of bifurcation stents and stent delivery systems by minimizing torque storage and by minimizing wire wrap which is a well known limitation of bifurcation delivery systems.

The torque bridge improves torque transmission and crossability by covering the balloon folds and applying elastic pressure to enhance column strength in this area of the balloon. The structural integrity of the balloon, which otherwise would have a limited ability to resist forces in circumferential direction, increases significantly and torque can be delivered through the balloon segment. Without the sleeve, the balloon (or inflatable shell) is virtually floating on the catheter attached to the distal shaft in one end and to the inner member at the distal tip. Therefore, torque cannot be efficiently delivered through this segment of the catheter. The sleeve is designed to compress the folds while still allowing the balloon to inflate and deflate during the deployment of the balloon and optionally to carry stents or other components or devices during the deployment. The sleeve will also reinforce the catheter shaft to improve axial force transmission and allow push forces to be transmitted all the way to the balloon to assist in overcoming obstacles. Such improved column strength and pushability is beneficial for the delivery of all types of stents including bifurcation stents which requires rotational alignment. In another embodiment the torque bridge is used for a stent delivery system of bifurcation stent with side branch apparatus or hole or crown that needs to be aligned to the side branch.

In one embodiment, the balloon catheter comprises a thin wall cylindrical polymer sleeve attached to the balloon's distal end and covers the balloon's distal taper and at least part of the balloon's working length, thus covering the balloon folds creating a smooth passage through difficult obstacles further improving crossability and handling. The sleeve can be made of elastic polymer such as pebax or polyurethane or nylon or alike and can be coated with lubricious coating to improve crossing. Further more, this polymer sleeve controls balloon inflation by creating an axial expansion movement in addition to the conventional radial expansion. This is particularly beneficial in treating side branch ostiums.

In one embodiment the balloon catheter comprises a thin wall polymer sleeve attached to the balloon's proximal end and covers the balloon's proximal taper and at least part of the balloon's working length. This "torque bridge" allows improved torque delivery all the way to the balloon by elastically constraining the proximal balloon pleats and eliminating the "candy wrap' effect thus enhancing the control of the operator. This novel design of the "torque bridge" enabling rotation of the beveled tip offers enhanced crossing abilities and overcoming obstacles.

In one embodiment of this invention, the balloon catheter comprises of a small ("football shaped") balloon typically with a working length of 3 to 6 mm sometimes with total lengths of 10 mm, 15 mm, or longer. In specific examples, the balloon will have distal and proximal tapers having lengths of 2.5 mm to 4 mm on either side of the working length in the middle. This balloon can be used to dilate a bifurcation ostium without slipping due to axial reinforcement of the torqueable catheter shaft. A middle or mid-line radiopaque marker will usually be provided on the balloon or shaft underlying the balloon to permit alignment of the balloon with the ostium and/or the stent wall prior to balloon inflation.

In another embodiment the combination of beveled tip and torque bridge is used for long balloons for peripheral applications to improve crossing through diffused and calcified lesions by allowing the operator to torque the catheter and navigate the asymmetric tip through the lesion(s).

Thus, in a first aspect of the present invention, a balloon catheter with improved crossing characteristics comprises a catheter body having a distal end, a proximal end, and an inflatable lumen near the distal end. A distal tip of the catheter body is asymmetrically beveled relative to an axis of the catheter body and at least a distal portion of the catheter body is torsionally reinforced to improve the ability to rotate the beveled tip by torquing a proximal end of the catheter body when the catheter is present in the vasculature. The beveled tip may be a simple planar bevel at an angle relative to the axis of the catheter in the range from 25° to 75°, usually at an angle in the range from 30° to 60°. Optionally, the catheter tip may be tapered one or more times between the maximum diameter region of the catheter body and the distal tip which is beveled. The distal tip may be beveled along two, three, four or more surfaces so that the tip resembles a diamond or trocar tip. The beveled tip without torque reinforcement is not functional in crossing lesions and may even be inferior to regular tip since its structural integrity is lower than regular tip (less materials and the distal end of the tip) and it may deform. Coupling this tip with torque reinforcement allows new way of crossing obstacles that was never used with balloon catheters due to the inability of the inflatable shell to deliver torque.

Torsional reinforcement of the catheter may include a variety of structures. In a first exemplary structure, a distal region of the catheter, typically at least over or within the balloon, may comprise a reinforcement sleeve. For example, an elastic reinforcement sleeve may cover a distal region of the balloon, a proximal region of the balloon, or in some cases the entire balloon. The elastic sleeve will not only provide additional column strength, thus increasing the torsional rigidity of the distal region of the catheter, it will also smooth the exterior surface of the catheter presented to the blood vessel and stent or other obstructions as the catheter is being advanced. In this way, the folds and discontinuous surface of the balloon may be covered and protected against engaging the stent struts or other obstructions. Alternatively or additionally, the stent body within the balloon may be reinforced by conventional structures, such as braids, coils, axial reinforcement elements, or the like. As an alternative to the elastic sleeves, the sleeves may be non-elastic or non-distensible but frangible so that they split, fracture or rupture as the balloon is inflated. In some instances, the balloon will have a particularly short length, typically from 3 mm to 6 mm, so that it may be inflated within a stent wall (typically within a single stent cell) to open the stent cell, while only a short portion of the balloon extends into the side branch and a similarly short portion of the balloon remains within the lumen of the stent in the main vessel. Such short stents have greatly improved the ability to dilate the ostium at the bifurcation. Preferably, the short balloons will have a radiopaque marker at or near their midsections so that the balloon can be aligned with the stent wall and/or the side vessel ostium prior to inflation.

In another aspect of the present invention, the catheters described above may be used for advancing the catheter tip past obstructions present within a patient's vasculature. The distal end of the catheter may be observed fluoroscopically as it is being advanced through the vasculature. If the stent encounters an obstruction, such as a stent strut, when attempting to enter a side branch vessel from a main branch vessel, the user may torque the stent from the proximal end, causing the beveled distal end to rotate and change its orientation relative to the obstruction. By continuing to rotate the stent and gently advance the stent, an orientation which allows the stent to atraumatically pass the obstruction will usually be found, and the catheter can be advanced forward. In some instances, after the balloon on the catheter is disposed within the cell of the stent, the balloon may be expanded to expand the stent cell.

In yet another aspect of the present invention, a balloon catheter having improved stent crossing characteristics comprises a catheter body having a distal end, a proximal end, and an inflatable balloon near the distal end. The balloon will have a short length, typically in the range from 3 mm to 6 mm, and a radiopaque marker at its middle. The balloon is preferably non-distensible and has a diameter in the range from 1 mm to 5 mm when fully inflated. This balloon may be used in methods for opening a cell in a stent deployed in a main branch vessel of a patient's vasculature. The method comprises advancing the short balloon into a cell adjacent to a side branch vessel so that the radiopaque marker is aligned with the cell or the ostium and a distal half of the balloon is advanced into the branch vessel and a proximal half of the balloon remains within a central lumen of the stent. After properly positioning the balloon, the balloon is inflated to open the stent cell.

BRIEF DESCRIPTION OF THE DRAWINGS

FIG. 1A shows a prior art catheter. FIGS. 1B-1C show a catheter according to the present invention, comprising a beveled or skived catheter tip, approaching the stent strut.

DETAILED DESCRIPTION OF THE INVENTION

The present inventions provides catheters and methods for their use with the improved ability to cross obstructions as they are advanced through a patient's vasculature, particularly the coronary vasculature. Obstructions which can be overcome by the catheters and methods of the present invention include tight turns, eccentric occlusions, and most particularly, stent struts present at a bifurcation. As discussed earlier, one or more struts which form part of a main vessel stent placed at a vessel bifurcation will often be located across the ostium leading into the side or branch vessel. The catheters and methods of the present invention are able to advance past such jailing stent struts in at least most cases.

The catheters and methods of the present invention may comprise and utilize various design elements which facilitate the catheter passage through obstructions. A first design element includes a beveled distal tip at a leading end of the catheter. The bevel will generally include at least one planar surface or face disposed at an angle in the range from 30° to 60° relative to a central longitudinal axis of the catheter, usually in the range from 40° to 50° relative to the axis. Optionally, the distal tip may include two or more of such inclined or beveled surfaces. A second design element of the catheter comprises torsional reinforcement over at least a distal portion of the catheter, typically over at least a distal or proximal portion of the balloon of the catheter. A third design element of the catheter is the use of a short balloon, typically in the range from 3 mm to 6 mm, which is particularly useful for expanding a cell or other aperture and its stent which is aligned with the ostium of a bifurcation. Such short balloons will preferably have a middle or a mid-line marker, typically a radiopaque marker on the catheter shaft, to facilitate positioning the short catheter at the ostium or within the struts of a stent adjacent the ostium.

Figure 1A:
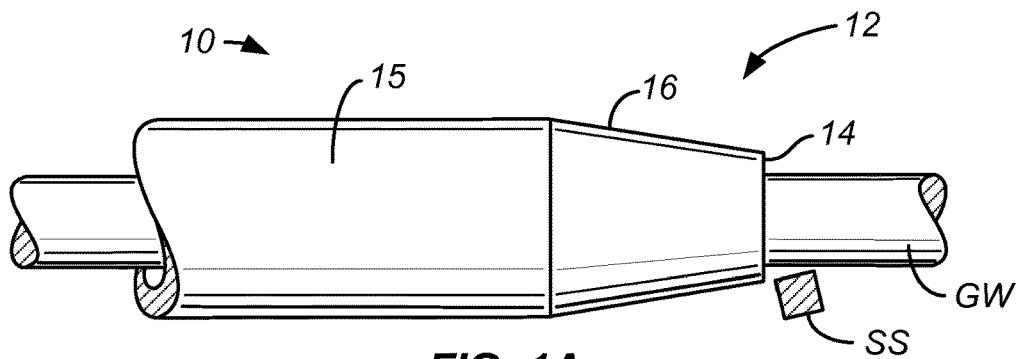
FIGS. 1A to 1D show catheter tips approaching a stent strut.

Referring to FIG. 1A, a prior art balloon catheter 10 would typically have a distal end or tip 12 with a blunt leading edge 14 which is oriented at 90° relative to the longitudinal axis 15 of the catheter. In order to facilitate advancement, such catheters would often have a distally converging taper 16, typically a conical section, but because of the limitations of catheter fabrication described above, the blunt leading edge 14 would still present a square as shoulder the catheter is advanced over the guidewire GW. The shoulder would create a substantial risk of catching or engaging a stent strut SS or other luminal obstruction, thus compromising the ability to advance the catheter through the vasculature or other body lumen, and particularly through side branch ostia covered by stents.

Figure 1B:
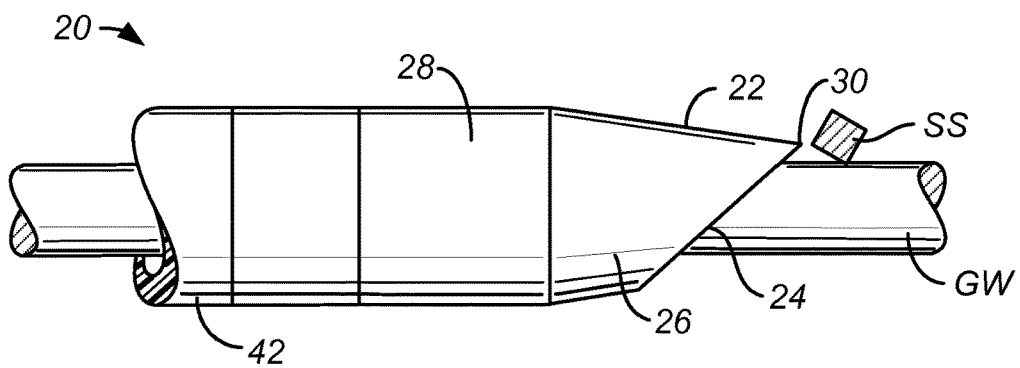
Figure 1C:
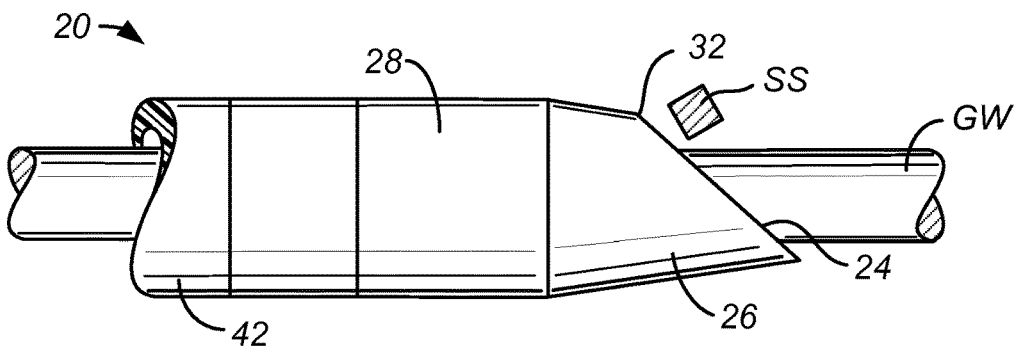

Referring now to FIGS. 1B and 1C, a catheter 20 constructed in accordance with the principles of the present invention will have a distal tip 22 having a beveled leading edge 24. The beveled leading edge is typically formed at the distal end of a tapered or conical section 26 located distal to the main body 28 and balloon 42 (shown schematically) of the catheter.

The beveled leading edge 24 of catheter 20 can still engage or catch stent struts SS as the catheter is advanced through the wall of a stent disposed at a side branch ostium, particularly if the distalmost tip 30 is rotationally aligned engage the stent strut, as shown in FIG. 1B. In contrast to the prior art catheter 10, however, the catheter 20 of the present invention allows the user to rotate the catheter body about the guidewire GW so that another portion of the leading edge 24, such as the trailing surface 32 of the leading edge engages the stent strut SS, as shown in FIG. 1C. The trailing edge, which trails away from the direction of advancement, allows the stent to easily move past the stent strut SS and into the branch vessel.

Figure 1D:
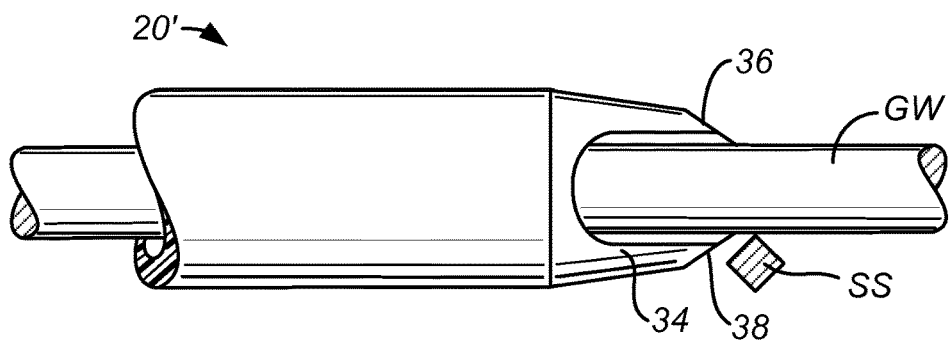

Although the beveled leading edge 24 will preferably consist of a single surface having generally planar geometry (other than the aperture or opening for passing the guidewire) as illustrated in FIGS. 1B and 1C, it is also possible to provide a catheter 20 having a plurality of beveled or inclined surfaces 34, 36, and 38, as illustrated in FIG. 1D. The distal tip, which then resembles a trocar cutting element having a plurality of facets, is even less likely to engage and interfere with the stent strut SS, although it is still possible to rotate the catheter should any difficulty be encountered in moving the catheter past the stent strut.

The balloon tip can be beveled at various angles, preferable lower then 65 degrees and optimally at about 45-30 degrees. Bevel angle is measured between the beveled surface and the longitudinal axis of the catheter. It can be done on one side or both sides (FIG. 1D) to prevent bias of the tip. If the angle is too steep (e.g., lower than 30 degree) the un beveled area is too long and can bend out when interfering with obstacles thereby creating risk of tip deformation, dislodgment and patient safety. If the angle is not steep enough (e.g. less than 75 degree) the advantage of the bevel is insignificant as the front tip cross section will interfere with the obstacle similar to conventional tip design.

Figure 2:
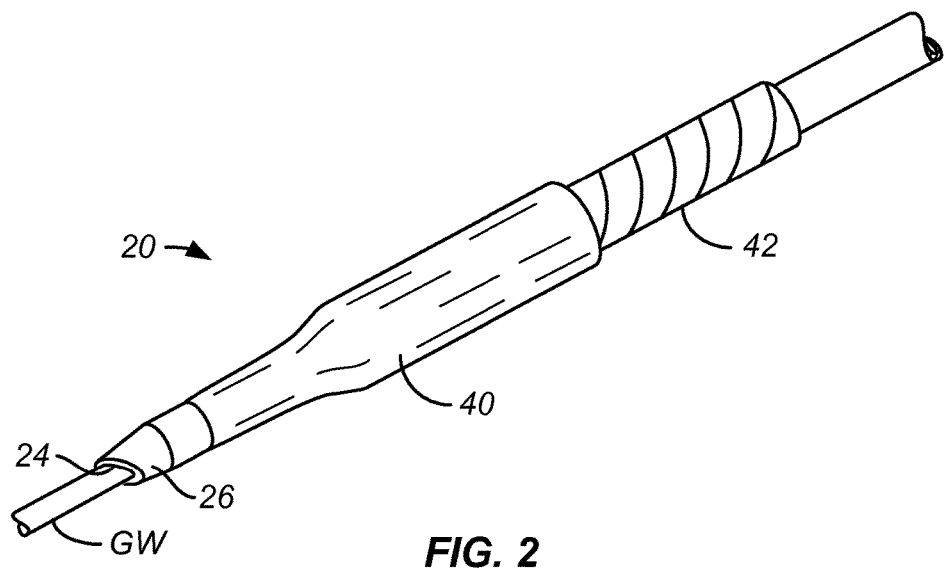
FIG. 2 shows a catheter of the present invention with a polymer sleeve that is attached over a distal portion of the balloon.

The catheter 20 will preferably have torsional reinforcement over at least a distal region of the catheter body. As shown in FIG. 2, an exemplary form of torsional reinforcement comprises a sleeve 40 formed over at least a distal portion of expandable balloon 42. The sleeve 40, which is typically elastic and has a smooth exterior surface, optionally having a lubricious film or coating disposed over the surface, will significantly reduce the risk that the folds of the balloon may interfere with or be captured by a stent strut or other obstruction as the catheter is advanced.

Figure 3A:
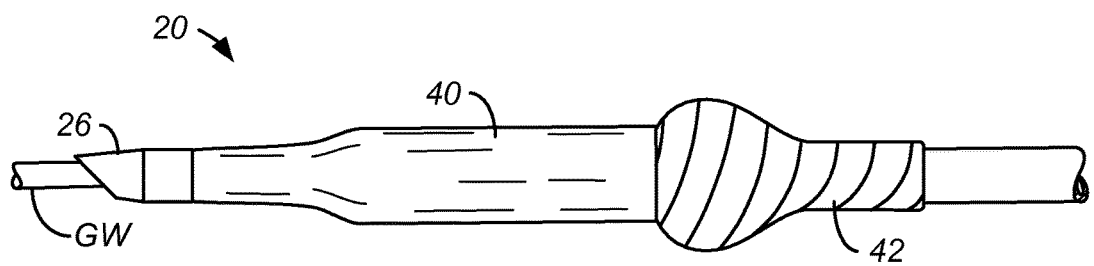
FIGS. 3A to 3B show an axially progressive expansion of the balloon catheter of FIG. 2.
Figure 3B:
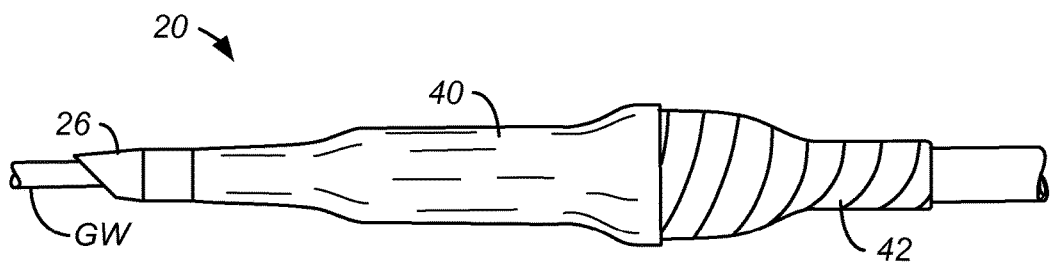

Inflation of the balloon 42 is illustrated in FIGS. 3A and 3B, where the balloon first expands in a proximal portion not covered by the sleeve 40. As the proximal portion fully inflates, the inflation "front" reaches the sleeve, which then inflates from its proximal end, as shown in FIG. 3B, toward the distal end. Upon deflation, the elastic sleeve 40 helps close and deflate the balloon. Thus, not only does the sleeve 40 help with introducing the balloon catheter, it can also facilitate with removing the balloon catheter.

The sleeve 40 need not be elastic, and in other embodiments could be inelastic or non-distensible. In such cases, the inelastic sleeve will typically have a frangible line or portion which permits it to split, rupture, or fracture upon balloon inflation. In order to facilitate withdrawal, the split sections could be adhered to the balloon surface so that they close with deflation of the balloon. In other instances, it may be desirable to cover the entire balloon with an elastic or inelastic sleeve, and in all cases, the sleeve will add to the column strength and torsional stiffness of the distal portion of the balloon section of the catheter. Such increased strength and stiffness combined to enhance the resistance to bending and to torsional buildup. Together, increased resistance to bending and torsional buildup will increase the efficiency of delivering the axial forces from a proximal end of the catheter to the distal end to overcome the obstruction of the stent strut or other materials.

The ability to progressively inflate the balloon from a proximal end toward a distal end can have particular advantage, when opening a stent or otherwise treating a side branch ostium. When treating a bifurcated lesion, it is common to dilate the ostium after stent deployment by positioning a distal end of the balloon in the side branch and a proximal end of the balloon in the main vessel. The balloon is inflated to dilate the ostium and position the stent struts outwardly toward the side branch in order to cover and "scaffold" the ostium. In practice, however, this procedure often pushes struts which are located distally to the balloon back into the main vessel rather than into the side branch. By progressively inflating the balloon from proximal to distal, as illustrated in FIGS. 3A and 3B, the distally advancing inflation of the balloon will push all the struts distally into the side branch, thus decreasing the risk that struts will protrude into the main vessel when the procedure is over.

Figure 4A:
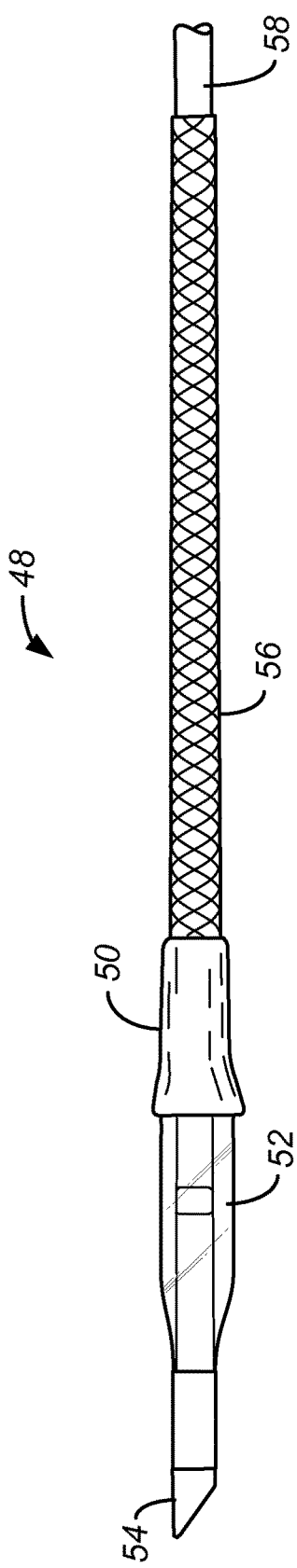
FIGS. 4A to 4B show a catheter of the present invention having a polymer sleeve attached over a proximal portion of the balloon in accordance with the present invention.
Figure 4B:
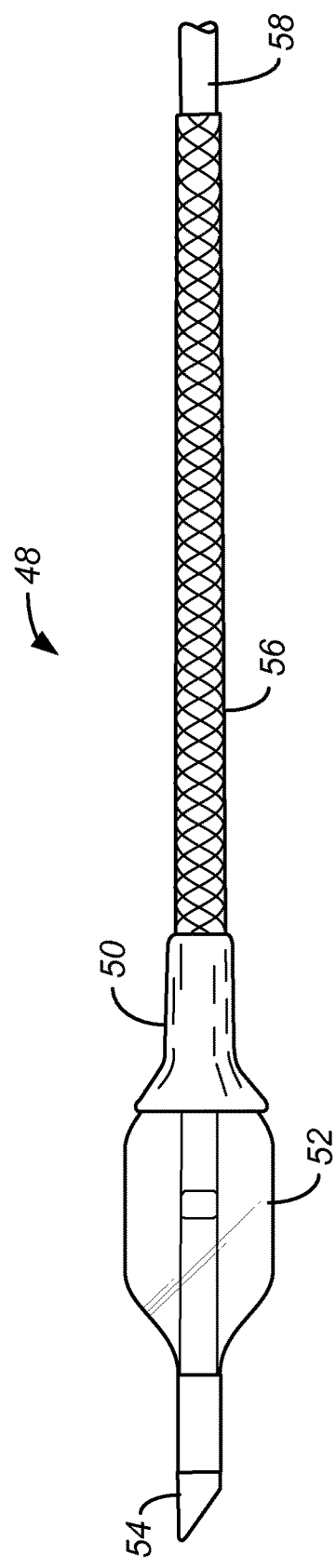

As illustrated in FIGS. 4A and 4B, the present invention also provides for placing a constraining sleeve over a proximal portion of the balloon. In particular, a sleeve 50 which may be elastic or inelastic as described above, covers a proximal taper of the balloon 52 of catheter 48 in order to cover the pleats of the folded balloon and inhibit the balloon from catching on the struts of a stent, particularly as the catheter is withdrawn through the stent. The sleeve 50 is preferably formed from an elastic material which can recover to close a balloon and the balloon is deflated. Thus, when the procedure is over, the proximal region of the balloon will be constrained and a smooth surface presented as the catheter is withdrawn. The proximal balloon 50 also enhances both torsional stiffness and column strength, a feature which is particularly useful when the balloon is adapted to deliver stents. In preferred embodiments, catheter 48 of FIGS. 4A and 4B will be combined with a beveled distal tip 54 and optionally a braided proximal shaft portion 56 in order to further enhance torsional stiffness and column strength. In the exemplary embodiments, the braided shaft section 56 may be attached to a proximal shaft 58 which may be a hypotube, conventional polymeric balloon catheter shaft, or the like.

Figure 5A:
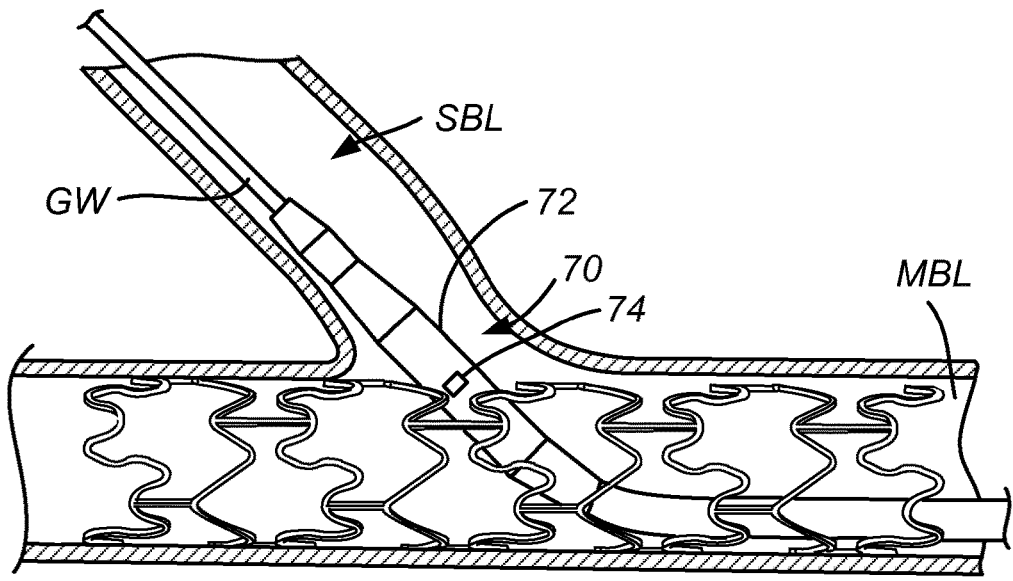
FIGS. 5A and 5B show expansion of a short balloon with a stent cell at a vascular bifurcation in accordance with the present invention.
Figure 5B:
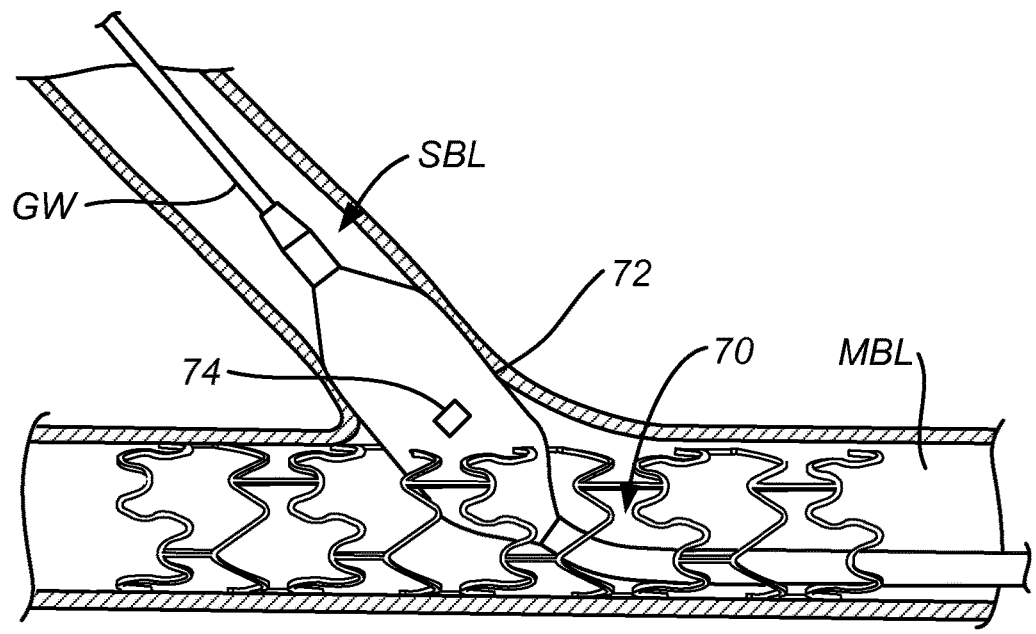

Referring now to FIGS. 5A and 5B, a balloon catheter 70 carries a short balloon 72 having a length less than 12 mm, usually less than 8 mm, and typically in the range from 3 mm to 6 mm. The balloon catheter 70 usually carries a radiopaque marker 74 at the approximate middle or mid-line of the balloon (middle of the axial dimension of the inflated balloon). Typically, the marker 74 is carried on the shaft within the balloon and will be visible under fluoroscopy to allow the middle of the balloon, i.e. the marker, to be positioned at the ostium or stent wall before inflation. When thus positioned, a distal half of the balloon is positioned largely within the side branch vessel lumen SBL, while a proximal half of the balloon remains largely in the main branch vessel lumen MBL. As the ostium is usually larger than the side branch vessel diameter, typically by about 0.5 mm, long balloons will generally enter the side branch increasing the risk of overdilation when the user is attempting to dilate stenotic material located at the ostium (which is a very typical occurrence). Use of the short balloons of the present invention minimizes the risk of overinflation of the side branch vessel.

While short balloons have been proposed in the past for a variety of purposes, their use in dilating the ostium of a bifurcation was hindered by their tendency to slip from the ostium back into the larger main vessel lumen. By inflating the short balloons of the present invention so that the midsection is in the ostium and preferably located within the stent structure, the balloon will be stabilized and held in place by the stent.

A further advantage of the short balloon is that it does not extend far into either the main branch vessel lumen MBL or side branch vessel lumen SBL. Longer balloons which extend proximally back into the main branch will tend to straighten as they are inflated. As the proximal end of a long balloon can be anchored within the main branch vessel, such straightening will then deflect the distal end of the balloon downward, thus preferentially opening struts on one side of the ostium and potentially causing an uneven dilatation.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A balloon catheter having improved crossing characteristics, said catheter comprising:
    a catheter body having a distal end, a proximal end, and a distal tip asymmetrically beveled relative to an axis of the catheter body, wherein the catheter body is torsionally reinforced over at least a portion thereof to improve rotation of the beveled tip when the catheter body is in the vasculature;
    an inflatable balloon near the distal end of the catheter body, the inflatable balloon having a distal portion and a proximal portion;
    a radiopaque marker disposed on the catheter body and underlying a middle portion of the inflatable balloon between the proximal and distal portions thereof; and
    a sleeve fixedly attached to at least an end of the balloon and covering at least a portion of the balloon to control expansion of the balloon, the sleeve applying elastic pressure to enhance column strength and torsional stiffness of the catheter body and the covered portion of the balloon at least when collapsed,
    wherein the catheter body is made of a thin wall polymer material,
    wherein the catheter body comprises a constant diameter braided shaft section to enhance torsional stiffness and column strength of the thin wall polymer material, and
    wherein the sleeve controls expansion of the balloon by covering at least the distal portion of the inflatable balloon to cause the inflatable balloon to progressively expand from a proximal end thereof to a distal end thereof when inflated.

2. A balloon catheter as in claim 1, wherein the sleeve is configured to present a smooth forward-facing surface to the vasculature as the catheter is advanced through the vasculature.

3. A balloon catheter as in claim 1, wherein the sleeve is elastic to expand and contract over the balloon as the balloon is inflated and deflated.

4. A balloon catheter as in claim 1, wherein the sleeve splits as the balloon is inflated.

5. A balloon catheter as in claim 1, wherein the balloon is non-distensible and has a diameter in the range from 1 mm to 5 mm, inclusive, when fully inflated.

6. A balloon catheter as in claim 1, wherein the balloon when inflated has a length in the range from 3 mm to 6 mm, inclusive.

7. A balloon catheter as in claim 1, wherein the catheter body comprises a catheter shaft and the radiopaque marker is disposed on a portion of the catheter shaft underlying the middle portion of the inflatable balloon.

8. A balloon catheter as in claim 1, wherein the sleeve is fixedly attached to a distal end of the balloon.

9. A balloon catheter as in claim 1, wherein the sleeve is fixedly attached to a proximal end of the balloon.

10. A balloon catheter as in claim 1, wherein the sleeve is configured to expand over the balloon as the balloon is inflated.

11. A balloon catheter having improved crossing characteristics, said catheter comprising:
    a catheter body having a distal end, a proximal end, and a distal tip, wherein the catheter body is torsionally reinforced over at least a portion thereof;
    an inflatable balloon near the distal end of the catheter body, the inflatable balloon having a distal portion and a proximal portion;
    a radiopaque marker disposed on the catheter body and underlying a middle portion of the inflatable balloon between the proximal and distal portions thereof; and
    a sleeve fixedly attached to at least an end of the balloon and covering at least a portion of the balloon to control expansion of the balloon, the sleeve applying elastic pressure to enhance column strength and torsional stiffness of the catheter body and the covered portion of the balloon at least when collapsed, and
    wherein the sleeve controls expansion of the balloon by covering at least the distal portion of the inflatable balloon to cause the inflatable balloon to progressively expand from a a distal end thereof the distal end thereof when inflated.

12. A balloon catheter as in claim 11, wherein the sleeve is configured to present a smooth forward-facing surface to the vasculature as the catheter is advanced through the vasculature.

13. A balloon catheter as in claim 11, wherein the sleeve is elastic to expand and contract over the balloon as the balloon is inflated and deflated.

14. A balloon catheter as in claim 11, wherein the sleeve splits as the balloon is inflated.

15. A balloon catheter as in claim 11, wherein the balloon when inflated has a length in the range from 3 mm to 6 mm, inclusive.

16. A balloon catheter as in claim 11, wherein the balloon is non-distensible and has a diameter in the range from 1 mm to 5 mm, inclusive, when fully inflated.

17. A balloon catheter as in claim 11, wherein the catheter body is made of a thin wall polymer material, and wherein the catheter body comprises a braided shaft section to enhance torsional stiffness and column strength of the thin wall polymer material.

18. A balloon catheter as in claim 17, wherein the braided shaft section has a constant diameter.

19. A balloon catheter as in claim 11, wherein the catheter body comprises a catheter shaft and the radiopaque marker is disposed on a portion of the catheter shaft underlying the middle portion of the inflatable balloon.

20. A balloon catheter as in claim 11, wherein the sleeve is fixedly attached to a distal end of the balloon.

21. A balloon catheter as in claim 11, wherein the sleeve is fixedly attached to a proximal end of the balloon.

22. A balloon catheter as in claim 11, wherein the sleeve is configured to expand over the balloon as the balloon is inflated.

\* \* \* \* \*